United States Patent [19]

Gressel et al.

[11] Patent Number: 5,075,104
[45] Date of Patent: Dec. 24, 1991

[54] OPHTHALMIC CARBOXY VINYL POLYMER GEL FOR DRY EYE SYNDROME

[75] Inventors: Philip D. Gressel, Everman; Robert E. Roehrs, Forth Worth, both of Tex.

[73] Assignee: Alcon Laboratories, Inc., Ft. Worth, Tex.

[21] Appl. No.: 597,983

[22] Filed: Oct. 15, 1990

Related U.S. Application Data

[63] Continuation of Ser. No. 332,253, Mar. 31, 1989, abandoned, which is a continuation of Ser. No. 908,468, Dec. 5, 1986, abandoned, which is a continuation of Ser. No. 695,364, Jan. 23, 1985, abandoned.

[51] Int. Cl.$^5$ .................... A61K 31/765; A61K 31/78
[52] U.S. Cl. .................... 424/78.04; 514/915; 514/912
[58] Field of Search .................... 424/78, 81; 514/912, 514/913, 914, 915

[56] References Cited

U.S. PATENT DOCUMENTS

| | | | |
|---|---|---|---|
| 4,003,991 | 1/1977 | Krohn et al. | 424/81 |
| 4,008,321 | 2/1977 | Kamishita et al. | 424/243 |
| 4,271,143 | 6/1981 | Schoenwald et al. | 424/78 |
| 4,343,787 | 8/1982 | Katz | 424/78 |
| 4,407,792 | 10/1983 | Schoenwald et al. | 424/81 |
| 4,521,414 | 6/1985 | Chiou et al. | 514/229 |

FOREIGN PATENT DOCUMENTS

1316556 9/1973 United Kingdom.
2007091 5/1979 United Kingdom.

OTHER PUBLICATIONS

CA 92: 220,622a (1980), Di Colo et al.
CA 93: 120,95611k (1983) Abd-Elbarz et al.
Handbook of Nonprescription Drugs-5th Ed.-1977, pp. 229-231 and 234-235.

*Primary Examiner*—Thurman K. Page
*Assistant Examiner*—E. J. Webman
*Attorney, Agent, or Firm*—James A. Arno; Gregg C. Brown; Julie J. L. Cheng

[57] ABSTRACT

Disclosed is an ophthalmic gel composition of unique rheological and lubricating properties comprising, inter alia, a carboxy vinyl polymer (carbomer) for use as a long lasting artificial tear. Also disclosed is a method of treatment comprising totally administering the composition when indicated for relief of dry eye syndrom, foreign body sensation, burning, hyperemia, corneal straining, and the like.

5 Claims, No Drawings

OPHTHALMIC CARBOXY VINYL POLYMER GEL FOR DRY EYE SYNDROME

This is a continuation of application Ser. No. 332,253 filed Mar. 31, 1989, which is a continuation of U.S. Pat. No. 908,468 filed Dec. 5, 1986, which is a continuation of Ser. No. 695,364 filed Jan. 23, 1985, which is based on International Application No. PCT/US 83/00840 filed May 25, 1983, now abandoned.

BACKGROUND OF THE INVENTION

The present invention relates to ophthalmic gel compositions for human and veterinary use comprising, inter alia, in an aqueous vehicle, a class of polyanionic polymers which, because of their unique combination of mucominetic, rheological, and lubricating properties, are useful as long lasting, topically applied agents for relief of dry eye syndrome, foreign body sensation, burning, hyperemia, corneal staining, and the like. The ophthalmic compositions are also useful as lubricating and cushioning agents for the eye after traumatic injury or surgery. They may also be used as corneal wetting and lubricating agents for use with contact lenses, and in various eye irritation disorders.

The present invention also relates to a method of treating eyes by topically applying the gel compositions of the present invention when indicated for the relief of dry eye syndrome and when indicated to achieve the other effects mentioned above. Dry eye syndrome, and related eye ailments, including mere transitory discomforts, are well known in the scientific and patent literature. The following patents are incorporated herein by reference to the extent that they provide additional background on the syndrome and recognized indications for its relief: U.S. Pat. Nos. 4,039,662; 3,987,163; 3,920,810; 3,843,782; and 4,131,651; and Belgian Patent 844,544.

However, none of these prior art formulations meet all of the important criteria for an effective and long lasting treatment of dry eye syndrome, particularly the moderate to serve kerato-conjunctivitis sicca (KCS) patient. These prior art attempts fall into three categories corresponding to their physical state: liquids, anhydrous ointments, and solids. The solids are in the form of ocular inserts which slowly dissolve or erode to provide a thickened tear film. While these have the potential for providing longer term symptomatic relief than liquids, few patients are willing to persist in using them since they are difficult to insert and, once in place, tend to be uncomfortable, frequently themselves causing the foreign body sensation they were meant to treat. Prior liquid and ointment formulations, while giving the sensation of relief, are strictly palliatives without long-term effect.

Thus, the search for an easy to use (especially by infirmed patients via self-medication), long lasting (4 to 24 hours) ophthalmic preparation for treating the effects described collectively under the dry eye syndrome and having the ancillary utilities mentioned above continues.

DETAILED DESCRIPTION OF THE INVENTION

The ophthalmic formulations of the present invention are aqueous gels comprising, in addition to conventional ingredients imparting, for example, bacteriostatic and formulatory balance functions, a critical polyanionic polymer, and, in a preferred embodiment, a stabilizing agent therefor.

POLYANIONIC POLYMER COMPONENT

The high molecular weights polymers useful in the present invention have a molecular weight of from about 400,000 to about 6 million. The polymers are characterized as having carboxylic functional groups and preferably contain from 2 to 7 carbon atoms per functional group. The gels which form during the preparation of the ophthalmic polymer dispersion have a viscosity of from about 15,000 to about 300,000 cps (spindle 7) at 25° C. generated by an RVT Brookfield Viscometer, preferably from about 20,000 to about 200,000 cps. The viscosity of the gels is too high to be measured with a No. 3 spindle. The gels further are characterized as having a yield value of from about 1,500 to about 20,000 dyne/cm$^2$ or more as determined by a Ferranti-Shirley Viscometer at 25° C. The high molecular weight polymers used in the compositions of the present invention not only thicken the compositions to provide a gel, but they also provide a special type of rheology, i.e., plastic viscosity.

Plastic viscosity is indicative of a material that does not flow until a certain force or stress value is exceeded. This is referred to as the yield value. While not wishing to be bound by any theory, it is believed that the increased duration of activity of the gel compositions of the invention is related not only to the apparent viscosity (thickness), but is also related to the yield value. The gel compositions of the present invention exhibit unique response to shear stress. When the yield value is exceeded, the gel structure is altered temporarily, allowing the gel to flow under stress. In the eye, this corresponds to the blinking eyelid. When the stress is removed (eyelid at rest) the structure of the gel is partially re-established.

The high molecular weight polymers useful in the ophthalmic compositions of the present invention provide unique rheological characteristics, combining high viscosity with yield values at the levels set forth herein above. They confer lubricative properties, and are polyanionic in charge character owing to their carboxylic acid functional groups. While the claimed invention will not be limited by any theory of action, but in the sense of providing a functional definition, it will be noted that these polyanionic charged polymers appear to function by maintaining or restoring the normal hydration equilibrium of the epithelial cells, protecting the cornea in a manner similar to that believed to be provided by the mucin component of normal tears. Therefore, in theory, the polymers, in addition to being well retained in the eye and providing lubrication, can function as a mucin substitute in the dry eye syndrome where there is a deficiency or absence of the natural mucin component of the normal tears.

Suitable polymers useful in the present invention are carboxy vinyl polymers. Preferred polymers of this class include Carbomers, available under the trade name Carbopol from the B. F. Goodrich Company. The known and readily available polymers Carbopol 934 and 940 are specifically preferred. The polymers are used in the aqueous gel compositions at a level of from about 0.25% to about 8% by weight.

STABILIZING AGENT

Owing to the use of relatively high polymer content, a stabilizing agent may be required to maintain the hydration state of the polymer during long storage. While not imposing any limitation by theory of action, but in the interest of describing function, it should be noted that associations appear to occur within or among the polymer chains which, after time, favor the reduction of hydration state of the polymer chains. These may be in the form of hydrogen bonds within and among the polymer chains. This can manifest itself as a change in viscosity and texture of the gels. Agents which greatly decelerate or eliminate this aging process in the instant compositions of high polymer content are generically polyols at a concentration range of from 0.2% to 5% by weight. Representative of such polyols are mannitol, sorbitol, glycerol, sucrose, related sugars, and the like, in the above-recited concentration range. An especially preferred stabilizing agent is mannitol at a concentration of from 0.2% to 5% by weight.

OTHER INGREDIENTS

Antimicrobial Preservative: Ophthalmic products are packaged in multiple use containers as a general rule. Preservatives may be incorporated to prevent contamination of the products when they are exposed to microorganisms during use. One or more preservatives and ancillary agents may be chosen from, for example: benzalkonium chloride, thimerosal, chlorobutanol, methyl paraben, propyl paraben, phenylethyl alcohol, edetate disodium, sorbic acid, Onamer M (Onamer M is available from Onyx Chemical Company, Jersey City, N.J.), or other agents known to those skilled in the art. Typically such preservatives are employed at a level of from 0.001% to 1.0% by weight. If no preservative is desired, the gels may be sterile packaged in unit-of-use containers. With respect to the use of Onamer M, co-pending, commonly assigned U.S. Patent application Ser. No. 306,317 filed Sep. 28, 1981, is incorporated herein by reference to the extent that it describes Onamer M.

Neutralizing Agents: The polyanionic polymers may be neutralized to the desired pH with basic chemicals such as sodium hydroxide, ammonium hydroxide, ethanolamine, urea, and selected amines. Mineral acids such as hydrochloric, phosphoric or sulfuric may be used to adjust pH toward acidity. The preferred pH range is from 4.5 to 8.5.

Tonicity Agents: The tonicity of the gels can be adjusted to either hypotonicity, isotonicity or hypertonicity relative to normal tears by use of generally used materials known to the art. Sodium chloride is a preferred tonicity agent. The stabilizing agents confer a proportion of the desired tonicity, or may provide sufficient tonicity so that no additional agents are required.

FORMULATION

The following compounding procedure may be used for sterile manufacturing. A dispersion of polymer is made in either purified water or a dilute acid solution. All other components are dissolved in purified water and added to the polymer dispersion. The dispersion is sterilized by autoclaving or by heating in a pressurized vessel to sterilizing temperature 121° C., for thirty minutes. The base is added aseptically by methods generally known to the art. The pH is measured and adjusted aseptically and the final weight is adjusted with sterilized purified water. Specific examples are detailed below.

PHYSICAL PROPERTIES

The viscosity, Brookfield RVT, measured at ambient room temperature, may be between 15,000 and 300,000 centipoises using spindle 7. Preferably the viscosity is between 20,000 and 200,000 centipoises using spindle 7 at 20 RPM. The viscosity is too high to measure with spindle 3. A further rheological property is that air bubbles are permanently suspended, except if they are removed by measures such as centrifugation or vacuum processing. Viscosity measurements are made after entrapped air is removed. The pH is between 4.5 and 8.5. The gel is clear or nearly clear, smooth, and homogeneous.

USE

The artificial tear gels represented by the present invention are intended for relief of dry eye syndromes, particularly kerato-conjunctivitis sicca. These symptoms include, inter alia, foreign body sensation, burning, and hyperemia. Additionally, these gels can halt the progress of the syndrome and reverse its effects including, in moderate to severe cases of dry eye, corneal staining, which is made evident by use of Rose Bengal or Fluorescein. The dosage regimen is typically 5–50 mg, preferably 5–15 mg, of gel squeezed from an ophthalmic tip of a container into the lower conjunctival sac of the affected eye. Frequency of dosing is variably dependent upon the severity of the syndrome. For severe cases dosing may occur four or more times per day. The frequency is reduced when signs of the disease state show improvement. At that time dosing may be as infrequent as one dose daily or once every two or three days.

The following Examples are intended to further illustrate, but not to limit, the compositions of the present invention.

EXAMPLE 1

|  | % by Weight | Amounts |
| --- | --- | --- |
| Carbopol 940 | 3.5 | 700 grams of slurry A (5% Carbopol) |
| Hydrochloric Acid | q.s. pH 7 | 13.3 ml of 1N from slurry A |
| Mannitol | 3 | 200 ml of solution B |
| Edetate Disodium | 0.01 |  |
| Benzalkonium Chloride (plus 10% compounding excess) | 0.008 | 8 ml of solution C |
| Sodium Hydroxide | q.s. pH 7 | 65 ml of 6N |
| Purified Water | q.s. ad 100 | q.s. ad 1000 grams |

A slurry is made in which 5% Carbopol is sifted into a dilute acid solution (1.9% of 1N HCl) using a propeller mixer to form a vortex. The slurry (A) is mixed until it is free from visible lumps. It is then filtered by pumping through a cartridge filter to remove small particles. Then it is autoclaved for 30 minutes at 121° C. and subsequently handled aseptically using methods known to the art. A stock solution (B) of 0.05% edetate disodium and 15% mannitol in purified water is prepared by heating to 60° C. and sterile filtering through a 0.22 micron membrane filter maintained at a warm temperature. The sterile-filtered solution is also maintained warm until its use. A stock solution (C) of benzalkonium chloride 1.1% in purified water is sterile filtered and handled aseptically.

The gel is compounded on a laminar-flow bench using aseptic technique. The slurry (A) is weighed into a tared mixing bowl. Solution C is added slowly with mixing. When it is well dispersed, solution B is incorporated and mixed well until the slurry is once again homogeneous. The pH is adjusted with 6N sodium hydroxide with constant mixing while the base is added. The final weight is adjusted to 1000 grams with sterile purified water. The gel is once again mixed until it is homogeneous.

The Brookfield viscosity is obtained by centrifuging a sample of the gel to remove visible air bubbles. Spindle 7 is inserted carefully into the centrifuge tube and positioned appropriately. The 20 RPM setting is used. Viscosity measurements are 103,200 centipoises and 101,800 centipoises. The pH is 6.94. The appearance is that of a smooth, clear, self-supporting gel.

EXAMPLE 2

|  | % by Weight | Amounts |
| --- | --- | --- |
| Carbopol 940 | 0.75 | 450 grams of 5% Carbopol Slurry |
| Hydrochloric Acid | q.s. pH 7 | 8.55 ml of 1N from slurry A |
| Mannitol | 3 | 90 grams |
| Edetate Disodium | 0.01 | 0.3 grams |
| Benzalkonium Chloride (plus 10% compounding excess) | 0.008 | 0.264 grams |
| Sodium Hydroxide | q.s. pH 7 | 40 ml of 6N |
| Purified Water | q.s. ad 100 | q.s. ad 3,000 grams |

The procedure for compounding is similar to that in Example 1. The Brookfield viscosity, spindle 7, 20 RPM is 47,600. The initial pH is 7.02. The appearance is that of a smooth, clear, self-supporting gel.

EXAMPLE 3

|  | % by Weight | Amounts |
| --- | --- | --- |
| Carbopol 940 | 3.5 | 8,000 grams of 4.375% Carbopol |
| Hydrochloric Acid | q.s. pH 7.2–7.4 | 1.33 ml of 1N from slurry |
| Edetate Disodium | 0.01 | 1 gram |
| Sodium Chloride | 0.4 | 40 grams |
| Benzalkonium Chloride (plus 10% compounding excess) | 0.008 | 0.88 grams |
| Sodium Hydroxide | q.s. pH 7.2–7.4 | 835 ml of 6N + 20 ml of 1N |
| Purified Water | q.s. ad 100 | q.s. ad 10,000 grams |

The procedure is essentially the same as that in Example 1. A solution of 40 grams of sodium chloride and 1 gram of edetate disodium is made in 500 ml of water. A separate solution of benzalkonium chloride 1% is added, and the gel is completed as before. Brookfield viscosity, spindle 7, 20 RPM, is 97,900 centipoises. The pH is 7.24. The appearance is that of a smooth, clear, self-supporting gel.

EXAMPLE 4

|  | % by Weight | Amounts |
| --- | --- | --- |
| Carbopol 940 | 3.5 | 350 grams of 5% Carbopol |
| Hydrochloric Acid | q.s. pH 7 | 6.65 ml of 1N HCl from slurry |
| Edetate Disodium | 0.01 | 0.05 grams |
| Onamer M | 0.001 | 0.1 ml of 5% Solution |
| Sodium Hydroxide | q.s. pH 7 | 40 ml of 6N |
| Purified Water | q.s. ad 100 | q.s. ad 500 grams |

The procedure is essentially the same as Example 1. Brookfield viscosity is 142,000 centipoises. The pH is 7.0. The appearance is that of a smooth, clear, self-supporting gel.

What is claimed is:

1. An aqueous ophthalmic gel for the treatment of dry eye syndrome, consisting essentially of 0.25% to 8% by weight of a carboxy vinyl polymer having a molecular weight in the range of 400,000 to 6,000,000, and water, said gel having a yield value in the range of 1,500 to 20,000 dyne/cm$^2$.

2. The ophthalmic gel of claim 1, wherein the viscosity of the gel is in the range of 15,000 to 300,000 centipoise.

3. The ophthalmic gel of claim 1, wherein the viscosity of the gel is in the range of 20,000 to 200,000 centipoise.

4. The ophthalmic gel of claim 1, wherein the pH of the gel is in the range of 6.0 to 8.0.

5. The ophthalmic gel of claim 1, wherein the concentration of the carboxy vinyl polymer is in the range of 0.75% to 3.5% by weight.

* * * * *